United States Patent
Kahn et al.

(10) Patent No.: US 11,344,460 B1
(45) Date of Patent: May 31, 2022

(54) SLEEP QUALITY OPTIMIZATION USING A CONTROLLED SLEEP SURFACE

(71) Applicants: Philippe Richard Kahn, Santa Cruz, CA (US); Arthur Kinsolving, Santa Cruz, CA (US)

(72) Inventors: Philippe Richard Kahn, Santa Cruz, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 151 days.

(21) Appl. No.: 14/269,036

(22) Filed: May 2, 2014

Related U.S. Application Data (63) Continuation-in-part of application No. 13/622,325, filed on Sep. 18, 2012, now Pat. No. 10,463,300.

(60) Provisional application No. 61/536,532, filed on Sep. 19, 2011.

(51) Int. Cl.
*A61G 7/018* (2006.01)
*A61B 5/00* (2006.01)

(52) U.S. Cl.
CPC .......... *A61G 7/018* (2013.01); *A61B 5/4809* (2013.01)

(58) Field of Classification Search
CPC ....... A61B 5/6892; A61B 5/01; A61B 5/0255; A61B 5/0816; A61B 5/1118; A61B 5/4806; A61B 5/4818; A61B 5/7275; A47C 27/083; A47C 27/082; A47C 27/081; A47C 27/10; A47C 31/00; A47C 31/008; A47C 31/123; A47C 21/003; A47C 21/04; A61G 7/015; G05B 23/0267; G05B 11/011
See application file for complete search history.

(56) References Cited

U.S. PATENT DOCUMENTS

| | | |
|---|---|---|
| 5,928,133 A | 7/1999 | Halyak |
| 6,348,694 B1 | 2/2002 | Gershteyn et al. |
| 6,888,779 B2 | 5/2005 | Mollicone et al. |
| 8,398,546 B2 | 3/2013 | Pacione et al. |
| 8,770,742 B2 | 7/2014 | Howell et al. |
| 8,793,212 B2 | 7/2014 | McGuire |

(Continued)

FOREIGN PATENT DOCUMENTS

| | | |
|---|---|---|
| EP | 1139187 B1 | 10/2010 |
| WO | 2005092177 A1 | 10/2005 |

(Continued)

OTHER PUBLICATIONS

Iver, Conrad et al., The AASM Manual for the Scoring of Sleep and Associated Events: Rules, Terminology and Technical Specification, 1st ed., 2007, American Academy of Sleep Medicine, Wetchester, Illinois.*

(Continued)

*Primary Examiner* — Boniface Ngathi N
(74) *Attorney, Agent, or Firm* — Nicholson De Vos Webster & Elliott LLP; Judith Szepesi (57) ABSTRACT

A method and system to improve sleep quality. The system comprises a controller to control a temperature-controlled sleep surface, a temperature of the temperature controlled sleep surface adjusted, based on the user's sleep state and sleep quality, to improve the user's sleep quality. In one embodiment, the user's sleep state and sleep quality is determined based on data from monitoring system.

11 Claims, 9 Drawing Sheets

(56) References Cited

U.S. PATENT DOCUMENTS

| | | | | |
|---|---|---|---|---|
| 8,840,564 B2* | 9/2014 | Pinhas | ................ | A61B 5/0205 600/529 |
| 9,192,326 B2 | 11/2015 | Kahn et al. | | |
| 2004/0049132 A1 | 3/2004 | Barron et al. | | |
| 2004/0075549 A1 | 4/2004 | Haller | | |
| 2004/0133081 A1 | 7/2004 | Teller et al. | | |
| 2004/0149921 A1 | 8/2004 | Smyk | | |
| 2004/0152957 A1 | 8/2004 | Stivoric et al. | | |
| 2005/0143617 A1* | 6/2005 | Auphan | ................ | A61B 5/08 600/26 |
| 2005/0154330 A1 | 7/2005 | Loree | | |
| 2005/0172311 A1 | 8/2005 | Hjelt et al. | | |
| 2005/0245839 A1 | 11/2005 | Stivoric et al. | | |
| 2005/0264752 A1 | 12/2005 | Howell et al. | | |
| 2006/0106275 A1* | 5/2006 | Raniere | ................ | A61M 21/02 600/26 |
| 2006/0202816 A1 | 9/2006 | Crump et al. | | |
| 2006/0293608 A1 | 12/2006 | Rothman et al. | | |
| 2007/0018832 A1 | 1/2007 | Beigel et al. | | |
| 2007/0186330 A1 | 8/2007 | Howell et al. | | |
| 2008/0052837 A1* | 3/2008 | Blumberg | ............ | A47C 23/002 5/727 |
| 2008/0117060 A1 | 5/2008 | Cuddihy et al. | | |
| 2008/0122616 A1* | 5/2008 | Warner | ................ | A61B 5/0002 340/541 |
| 2008/0234785 A1 | 9/2008 | Nakayama et al. | | |
| 2008/0234935 A1 | 9/2008 | Wolf et al. | | |
| 2008/0275349 A1* | 11/2008 | Halperin | ............ | A61B 5/0205 600/484 |
| 2008/0306351 A1* | 12/2008 | Izumi | ................... | A61B 5/113 600/300 |
| 2009/0069642 A1 | 3/2009 | Gao et al. | | |
| 2009/0147215 A1 | 6/2009 | Howell et al. | | |
| 2009/0203971 A1 | 8/2009 | Sciarappa et al. | | |
| 2010/0049008 A1* | 2/2010 | Doherty | ............... | A61B 5/0476 600/301 |
| 2010/0056947 A1 | 3/2010 | Holmes | | |
| 2010/0079294 A1 | 4/2010 | Rai et al. | | |
| 2010/0100004 A1* | 4/2010 | Van Someren | ...... | A61B 5/0008 600/549 |
| 2010/0170043 A1* | 7/2010 | Young | ................ | A61B 5/4806 5/706 |
| 2010/0174198 A1* | 7/2010 | Young | ................ | A47C 27/144 600/484 |
| 2010/0174199 A1* | 7/2010 | Young | ................ | A61B 5/0205 600/484 |
| 2010/0283616 A1 | 11/2010 | Ruhs et al. | | |
| 2010/0306711 A1 | 12/2010 | Kahn et al. | | |
| 2011/0010014 A1* | 1/2011 | Oexman | ............. | A47C 27/061 700/276 |
| 2011/0015467 A1* | 1/2011 | Dothie | .................... | A61B 5/11 600/26 |
| 2011/0015495 A1 | 1/2011 | Dothie et al. | | |
| 2011/0092780 A1 | 4/2011 | Zhang et al. | | |
| 2011/0152637 A1 | 6/2011 | Kateraas et al. | | |
| 2011/0190594 A1* | 8/2011 | Heit | ...................... | A61M 21/00 600/301 |
| 2011/0270052 A1 | 11/2011 | Jensen et al. | | |
| 2011/0298613 A1 | 12/2011 | Ayed | | |
| 2012/0103556 A1* | 5/2012 | Lee | ....................... | F24F 11/006 165/11.1 |
| 2012/0221254 A1 | 8/2012 | Kateraas et al. | | |
| 2012/0313272 A1 | 12/2012 | Fullam et al. | | |
| 2012/0316471 A1 | 12/2012 | Rahman et al. | | |
| 2012/0316932 A1 | 12/2012 | Rahman et al. | | |
| 2012/0317430 A1 | 12/2012 | Rahman et al. | | |
| 2013/0018284 A1* | 1/2013 | Kahn | ................... | G04G 13/026 600/595 |
| 2013/0072765 A1* | 3/2013 | Kahn | ...................... | A61B 5/01 600/301 |
| 2013/0124891 A1 | 5/2013 | Donaldson | | |
| 2013/0253950 A1* | 9/2013 | Vanderpohl, III | ..... | G16H 10/60 705/3 |
| 2013/0267791 A1* | 10/2013 | Halperin | .............. | A61B 5/6892 600/300 |
| 2014/0005502 A1* | 1/2014 | Klap | .................... | A61B 5/7282 600/301 |
| 2014/0018686 A1 | 1/2014 | Medelius et al. | | |
| 2014/0259433 A1* | 9/2014 | Nunn | ..................... | A47C 31/00 5/713 |
| 2014/0277822 A1* | 9/2014 | Nunn | ................... | A61B 5/6892 700/301 |
| 2015/0083934 A1 | 3/2015 | Richter | | |

FOREIGN PATENT DOCUMENTS

| | | | | |
|---|---|---|---|---|
| WO | 2006009830 A2 | 1/2006 | | |
| WO | 2008072168 A1 | 6/2008 | | |
| WO | WO-2009029899 A1 * | 3/2009 | .......... | A61M 5/1723 |
| WO | WO 2011161680 A2 * | 12/2011 | .......... | A61B 5/0836 |
| WO | WO-2012077113 A2 * | 6/2012 | .......... | A61B 5/7221 |
| WO | WO-2013150523 A1 * | 10/2013 | .......... | A61B 5/4833 |

OTHER PUBLICATIONS

"Direct Link Between Insulin, Core Body Temperature Discovered," Thaindian News, <http://www.thaindian.com/newsportal/health/direct-link-between-insulin-core-body-temperature-discovered_100277502.html>,Nov. 20, 2009, 3 pages.

"Metabolic Temperature Graph," Dr. Rind, <http://www.drrind.com/therapiE/metabolic-temperature-graph>, AccEsed Sep. 18, 2012, 5 pages.

"Monitoring Disparities in Chronic Conditions Study: The MDCC Study," <http://www.healthmetricsandevaluation.org/-Eearch/project/monitoring-disparitiE-chronic-conditions-study-mdcc-study>, AccEsed Sep. 7, 2012, 2 pages.

"SunMate Ultraviolet Light Intensity Meter," <http://www.naturEenergiE.com/uv_meter.htm#.UlpCP44qe-ghat>, AccEsed Oct. 26, 2012, 1 page.

"UV Sunsignals Sensors," <http://sunsignals.com/how-it-works/> Accessed Oct. 26, 2012, 2 pages.

Coyle, Shirley, et al., "Textile Sensors to Measure Sweat pH and Sweat-rate During Exercise," <http://doras.dcu.e/3636/1/Coyle_pervasive2009.pdf>, AccEsed Sep. 12, 2012, 6 pages.

PCT/US2012/056146, International Preliminary Report on Patentability, Date of Completion Jan. 6, 2014, 17 pages including 11 pages of annexes.

PCT/US2012/056146, International Search Report, dated Mar. 7, 2013, 7 pages.

PCT/US2012/056146, Written Opinion of the International Searching Authority, Date of Completion Jan. 6, 2014, 10 pages.

Plarre et al., "Automated Detection of Sensor Detachments for Physiological Sensing in the Wild", Wireless Health, Oct. 10, 2010, pp. 5-7.

"Control of skin cancer by the circadian rhythm", PNAS, vol. 108, No. 46, pp. 18790-18795, Nov. 2011 to Shelby et al.

\* cited by examiner

Fig. 8

SLEEP QUALITY OPTIMIZATION USING A CONTROLLED SLEEP SURFACE

RELATED CASES

The present invention is continuation-in-part (CIP) of U.S. patent application Ser. No. 13/622,325, filed on Sep. 18, 2012, which is related to and claims the benefit of the filing date of U.S. Provisional Application No. 61/536,532, filed on Sep. 19, 2011. These applications are incorporated herein in their entirety.

FIELD

The present invention is related to sleep optimization, and more particularly to controlling a temperature controlled sleeping surface using a monitor, to optimize user sleep quality.

BACKGROUND

Sleep is being recognized as one of the keys to health. As research continues to show, good quality sleep not only decreases illness and increases health, it also increases the quality of life.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A system to improve sleep quality is described. The system in one embodiment uses a controlled sleeping surface, such as a mattress, sleeping pad, blanket, whose characteristics can be adjusted. In one embodiment, the adjustable characteristics include temperature and firmness. In one embodiment, other aspects of the sleep surface may also be controlled. In one embodiment, the system also a monitoring system, which monitors the user's sleep phase and sleep quality. The monitoring system, in one embodiment, is a body-worn device, such as a wristband or armband. In another embodiment, the monitoring system may be a smart phone or other mobile device, which is in proximity to the user, but not worn. In another embodiment, the monitoring system may be integrated into the sleeping surface. In another embodiment, the monitoring system may be a camera, IR sensor(s), or other systems that can detect the user's movements or physiological condition. In one embodiment, the monitoring system is a distributed system using inputs from multiple devices. For example the monitoring system may include a wristband used to monitor the user's motions, a smart phone including a microphone to monitor sounds, the mattress to monitor the user's body temperature, etc.

The system adjusts the controlled sleeping surface, to support the user's sleep. In one embodiment, the system creates a feedback loop, with the controlled sleeping surface adjusted based on the immediate feedback from the monitoring system. The system enables the controlled sleeping surface to have a temperature and firmness, and optionally other state, which is optimized for the user's current sleep state, and next sleep state, or when needed, waking up. The system enables the user's sleep quality and quantity to be optimized, and the user to wake up refreshed.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

Figure 1A:
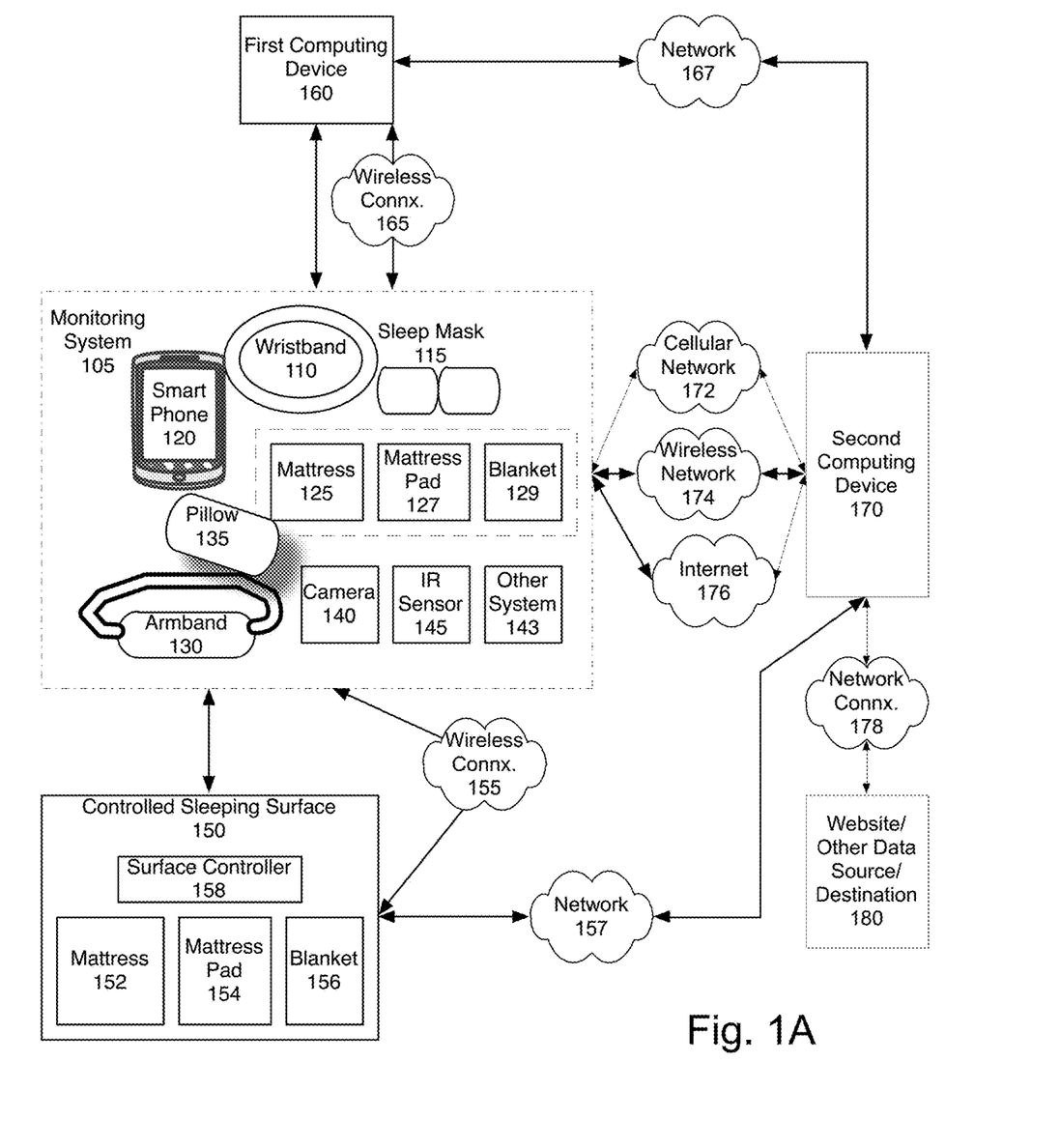
FIG. 1A is a diagram of one embodiment of the system.

FIG. 1A is a diagram of one embodiment of the system. The system includes, in one embodiment, a controlled sleeping surface 150, which may be a mattress 152, mattress pad 154, or blanket 156. The controlled sleeping surface 150 includes controls 158 that may alter the temperature, firmness, and/or other qualities of the sleeping surface.

In one embodiment, the controlled sleeping surface connects to a monitoring system 105. The monitoring system may, in one embodiment, be coupled to the controlled sleeping surface via a wireless or wired connection 155. In one embodiment, the monitoring system 105 may be integrated into the controlled sleeping surface 150.

FIG. 1A shows some exemplary monitoring systems 105, which include a wristband 110, armband 130, smart phone 120, IR sensor 145, camera 140, sleep mask 115, or other device. As noted, the monitoring system may also be part of the sleeping surface, e.g. a mattress 125, mattress pad 127, blanket 129, or pillow 135. Other systems 143 may also provide monitoring.

The monitoring system 105 may range from a simple sensor that detects when the user gets into the bed/onto the sleeping surface 150, to a complex system that monitors the user's motions, brainwaves, eye lid movements, galvanic skin response (GSR), body temperature, etc. The monitoring system 105 is designed to provide data to the controlled sleeping surface 150, to enable surface controller 158 to adjust the sleeping surface to optimize the user's sleep. In one embodiment, the controlled sleeping surface 150 includes a basic system that can adjust the sleeping surface according to a predetermined pattern, such that when a monitoring system 105 is not available, or the connection with the monitoring system 105 is interrupted, the sleeping surface 150 continues to be optimized for the predicted user sleep state.

In one embodiment, monitoring system 105 may be coupled, via a wired or wireless connection 165, to a first computing device 160. In one embodiment, the first computing device 160 may be a smart phone, personal digital assistant, tablet computer, or similar mobile device. In one embodiment, the computing device 160 may be a laptop or desktop computer.

In one embodiment, monitoring system 105 may be coupled, via a wired or wireless connection 172, 174, or 176, to a second computing device 170. In one embodiment, the second computing device 170 may be a smart phone, personal digital assistant, tablet computer, a laptop or desktop computer, or a remote service accessible through a network. In one embodiment, the monitoring system 105 may be coupled to second computing device 170 through first computing device 160 over a network 167.

In one embodiment, the controlled sleeping surface 150 may be coupled to the second computing device 170, via a network 157. The network may be a cellular network, a wireless network, or another type of network.

In one embodiment, the second computing device 170 may be coupled to other third party data sources 180, via a network connection 178. These third party sources may include websites, or other data sources or data destinations. For example, in one embodiment, the data destination 180 may be a manufacturer's reporting system, which may be used to monitor the safety and efficacy of the controlled sleeping surface 150 and/or monitoring system 105.

Although these elements are illustrated as separate components, it should be understood that they may all be integrated into a single system, and that the connections shown are merely exemplary. That is, in one embodiment, the controlled sleeping surface 150 may include a monitoring system 105 and a computing device 160, 170. Other configurations are possible. At its most basic, the system includes a method to detect a user laying down to go to sleep, and a controller to control at least one aspect of the controlled sleeping surface, based on the predicted sleep cycles of the user. At its most complex, a complete feedback cycle ensures that the user's current sleep cycle is identified by the monitoring system 105, and the controlled sleeping surface 150 is adjusted to optimize to the user's current sleep phase, and next necessary sleep phase.

Figure 1B:
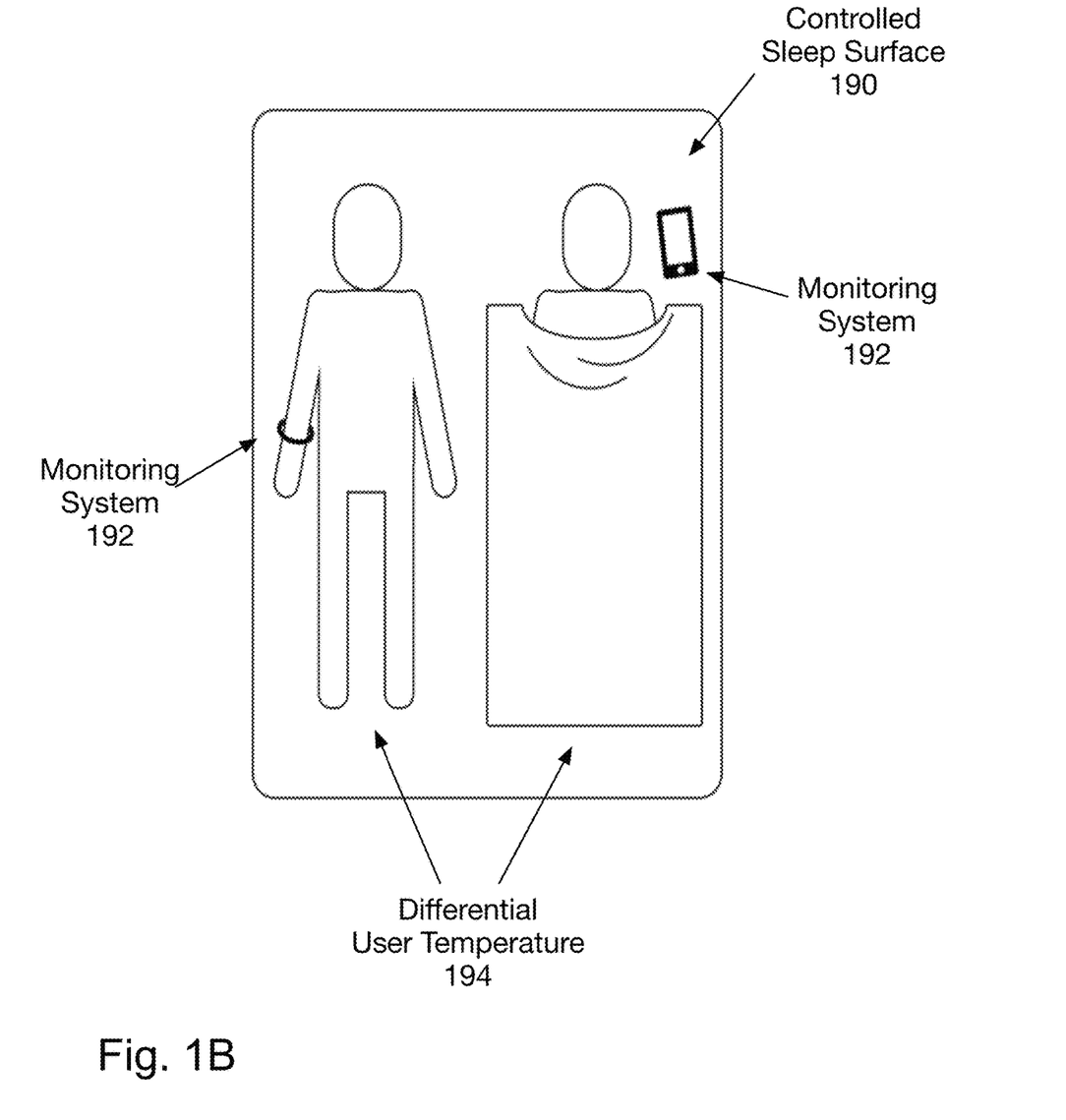
FIG. 1B is a diagram showing some exemplary scenarios.

FIG. 1B is a diagram showing some exemplary scenarios. Controlling a sleeping surface to optimize for a user's sleep quality can be complex. The figure shows two exemplary monitoring systems 192, a wrist band and a smart phone. Other types of monitoring systems may be used, of course. The users experience very different temperatures 194, because one has a blanket on and the other doesn't. Obviously, controlling the controlled sleep surface 190 should depend on not only the sleep state of the individual user but also the relative temperature of the user. The user under the blanket, for example, would need much less heat from the controlled sleep surface 190 to feel the same effective temperature as the user who is uncovered.

Furthermore, each user may have different personal preferences. Additionally, medical or physiological conditions may alter the optimal temperatures for a user.

In one embodiment, the system can account for variations between users based on user characteristics. Some exemplary user characteristics include gender, age, weight, height, and medical conditions. For example, a user who is going through menopause may have hot flashes. Adjusting for these hot flashes would allow the user to sleep through, instead of being woken up. Similarly, a user who has bad circulation may have particularly cold extremities, and may need additional heat to feel comfortable and sleep through the night.

Figure 2:
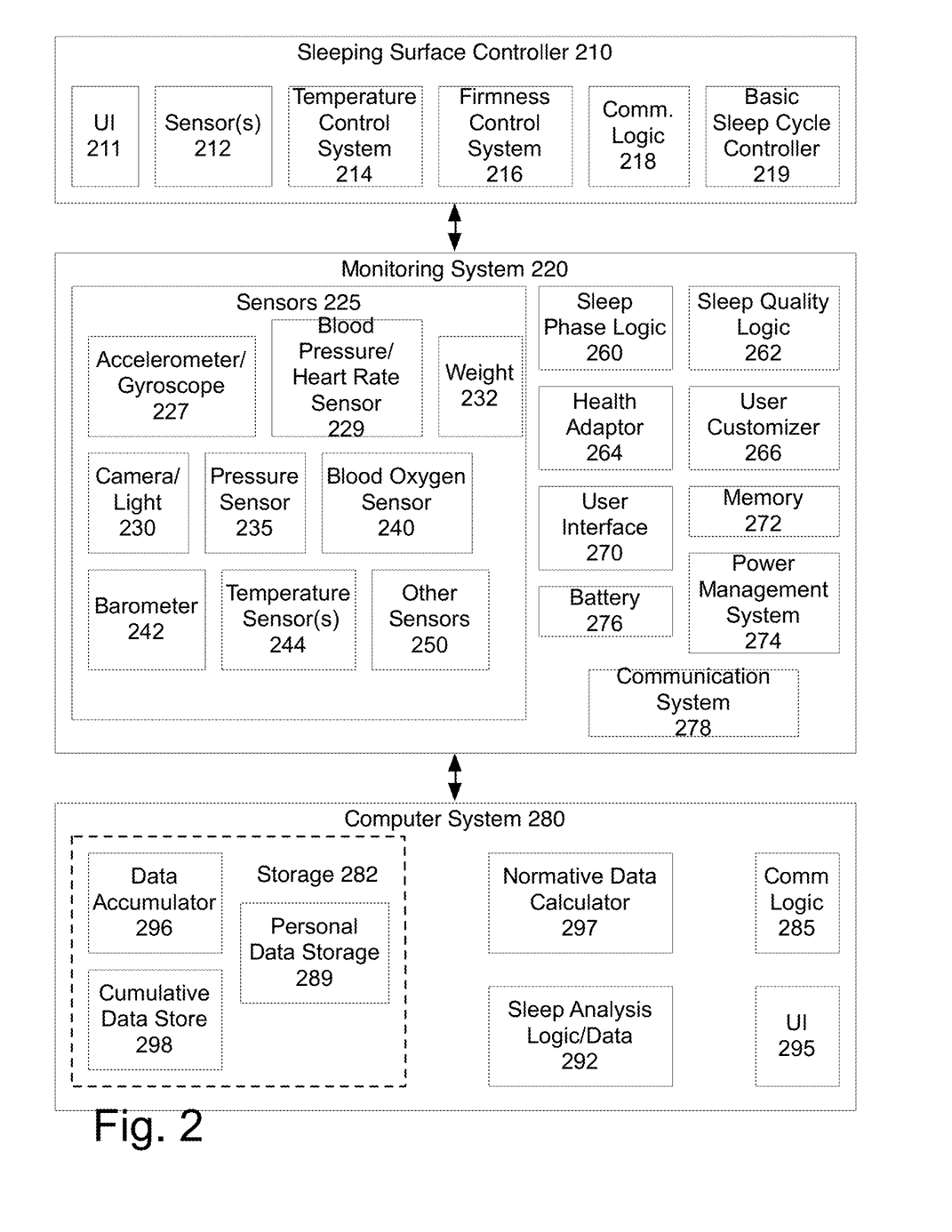
FIG. 2 is a block diagram of one embodiment of the system, including the sleeping surface control, monitoring system, and computer system.

FIG. 2 is a block diagram of one embodiment of the system, including the sleeping surface control, monitoring system, and computer system. The system, in one embodiment, includes sleeping surface controller 210, monitoring system 220, and computer system 280. In one embodiment, the sleeping surface controller 210 may be integrated with monitoring system 220, e.g. the monitoring system may be integrated into the sleeping surface. In one embodiment, monitoring system 220 may be integrated with computer system 280, e.g. a smart phone or another mobile device may act as both the monitoring system 220 and computer system 280.

Sleeping surface controller 210 may include, in one embodiment, sensors 212. Sensors 212 may be a proximity sensor, pressure sensor, weight sensor, motion sensor, other sensor integrated with the sleeping surface and/or sleeping surface controller 210 to sense that the user is on the controlled sleeping surface, or a user interface such as a switch or button, utilized by the user to indicate that he or she is going to sleep now.

In one embodiment, the sleeping surface controller 210 includes a basic sleep cycle controller 219, which enables the sleeping surface controller 210 to be self-contained, such that when the monitoring system 220 is disconnected or unavailable, the sleeping surface controller 210 can continue providing adjusted sleep surface optimized for the expected sleep phase. The basic sleep cycle controller 219 may receive input from sensors 212, and/or from a user interface 211, to identify the start time of the user's sleep cycle. The general sleep cycles for most users are similar, e.g. awake, light sleep, REM sleep, deep sleep, REM sleep, deep sleep, etc. The basic sleep cycle controller 219 uses a pre-calculated sleep rhythm. In one embodiment, the pre-calculated sleep rhythm is based on user characteristics, such as the user's age, gender, weight, height, etc. In one embodiment, the user enters these characteristics into the system. In one embodiment, it may be entered into a registration form on a website or the like, which transmits it to the sleeping surface controller 210. In another embodiment, this data may be obtained from the monitoring system, as described below.

The sleep surface adjustments, in one embodiment, are temperature control system 214 and firmness control system 216. In one embodiment, other aspects of the sleeping surface may be adjusted. In one embodiment, the temperature control system 214 and firmness control system 216 may be able to provide differential control for different portions of the mattress. In one embodiment, for a double or larger mattress, the sleeping surface controller 210 provides personalized control for each of the sleepers. In one embodiment, there may be differential temperature controls for a single sleeper vertically, e.g. a different temperature for the user's head, torso, legs, and feet. As illustrated in FIG. 2, the sleeping surface controller 210 may further include communication logic 218.

Monitoring system 220 includes sensors 225. The sensors 225 may include, one or more of: an accelerometer/gyroscope 227, blood pressure/heart rate sensor 229, camera/light sensor 230, weight sensor 232, pressure sensor 235, blood oxygen sensor 240, and barometer 242. In one embodiment, temperature sensor(s) 244 may also be included, as well as other sensors 250. The sensors 225 are used to identify the user, and to determine the sleep phase as well as the sleep quality of the user. In one embodiment, the monitoring system 220 includes a user interface where the user may indicate that he or she is going to sleep now.

In one embodiment, the monitoring system 220 can automatically identify the user, based on a combination or one or more of weight, blood pressure/heart rate, and movement patterns. This may be useful in a situation where there are multiple possible users of the sleep surface, such as spouses.

In one embodiment, the temperature sensor(s) 244 may monitor the user's body temperature as well as room temperature. This ensures that the temperature of the sleep surface reflects the user's actual body temperature. In one embodiment, this also enables the system to compensate for additional health issues, such as hot flashes accompanying menopause, fevers, etc.

Monitoring system 220 includes sleep phase logic 260, which uses data from sensors 225, and optionally sensors 212 in sleeping surface controller 210 to determine the user's current sleep phase, and whether user should be moving into the next sleep phase or not. The sleep phase logic 260 in one embodiment uses the systems described in co-pending application U.S. Ser. No. 13/545,963, entitled "Sleep Monitoring System," incorporated herein by reference. In one embodiment, sleep phase logic 260 also detects when the user falls asleep, e.g. enters the beginning of the first sleep cycle.

Sleep quality logic 262 in one embodiment uses sensor data, from sensors 225 and optionally 212, to determine the user's current sleep quality. Sleep quality is the depth of sleep, restlessness, and the match of the current sleep phase, as determined by sleep phase logic 260 with the optimal sleep phase cycle for the user.

In one embodiment, health adapter 264 identifies the changes in the optimal sleep phase, and sleeping surface control settings based on the user's health conditions. These health conditions may include temporary health conditions such as fevers, colds, or other illness, or more long-term issues such as hot flashes during menopause, poor circulation, or other issues. In one embodiment, the user may input such health conditions to the system via user interface 270. In another embodiment the health adaptor 264 may automatically detect certain conditions. For example, hot flashes are detectable based on body temperature fluctuations, in combination with the known age of the user. Similarly, fever can be identified based on a higher body temperature than normal, and the body temperature being in a certain range.

User customizer 266 customizes the sleep phase data, and sleeping surface control settings, based on the user's sleep data. In one embodiment, long-term sleep data is stored in memory 272. User customizer 266 uses that data, and optionally data from health adaptor 264, as well as detected data from sleep phase logic 260 to adjust the optimal sleep phases, and sleeping surface controls. In one embodiment, the user customizer 266 sends its data to the basic sleep cycle controller 219, in sleeping surface controller 210. This enables the sleeping surface controller 210 to provide a customized sleep cycle-adjusted sleep surface, even if the monitoring system 220 is not available.

In one embodiment, the monitoring system 220 includes power management system 274, and battery 276. The power management system 274 reduces power to the sensors 225 and the processor which controls sleep phase logic 260, sleep quality logic 262, health adaptor 264, user customizer 266, and communication system 278, based on whether the monitoring system 220 is currently in use, and the available battery charge. In one embodiment, data from sensors 225 may be provided to power management system 274, such that most of the monitoring system 220 can be turned off or set to a sleep state when the system is not in use.

In one embodiment, the system may maintain one or two sensors at a low test rate, when the monitoring system 220 is not in use, e.g. when the user is not on the sleeping surface. When the sensors detect that the user may have gotten onto the sleeping surface, the power management system 274 powers on the other sensors, and the processor(s) providing the analysis.

Communication system 278 enables communication between monitoring system 220, sleeping surface controller 210, and optionally computer system 280. In one embodiment, the communication system 278 may include a hardwired connection between monitoring system 220 and sleeping surface controller 210. Wireless, wired, or other communications may be encompassed within communication system 278.

In one embodiment, the communication between the monitoring system 220 and the sleeping surface 210 is not available, the basic sleep cycle controller 219 in sleeping surface 210 continues to adjust the controlled sleeping surface, based on the pre-calculated sleep rhythm. Thus, the controlled sleeping surface 210 provides a sleep-optimized surface, whether or not the monitoring system 220 is available. Additionally, in one embodiment, for intermittent connections, the basic sleep cycle controller 219 can maintain the current sleep rhythm, based on the prior data from the monitoring system 220.

In one embodiment, the system includes computer system 280. As noted above, computer system 280 may be a personal computer or remote server.

The computer system 280 provides storage 282. In one embodiment, data accumulator 296 receives data from one or more monitoring systems 220 and sleeping surface controllers 210, via communication logic 285. Cumulative data store 298 is the long-term storage, which in one embodiment stores user sleep data over the long term. In one embodiment this data may be useful for long-term user health analysis, as well as cumulative aging analysis.

Personal data storage 289 stores personally identifiable sleep data, whereas cumulative data store 298 stores abstracted data that cannot be used to identify a particular user, in one embodiment.

In one embodiment, computer system 280 provides sleep analysis logic/data 292, which may take over some or all of the calculations described as being performed by monitoring system 220. For example, in one embodiment, sleep analysis logic 292 on computer system 280 provides health adaptor 264 and user customizer 266 functionality.

Normative data calculator 297 calculates the baseline values for sleep phases for users. In one embodiment, normative data calculator 297 is used to populate the baseline data for monitoring system 220 and basic sleep cycle controller 219 in sleeping surface controller 210.

User interface 295 in one embodiment provides a richer interface for user to view their data, on a full size screen. In one embodiment, user interface 295 is accessible through a web interface or similar.

In one embodiment, the monitoring system 220 and/or the computer system 280 may additionally be used for monitoring the user's state throughout the day. One example of an integrated monitoring system that may be used as monitoring system 220 and also provide daytime monitoring is described in co-pending application U.S. Ser. No. 13/622,325, entitled "An Improved Body-Worn Monitor," which is incorporated herein by reference.

Figure 3:
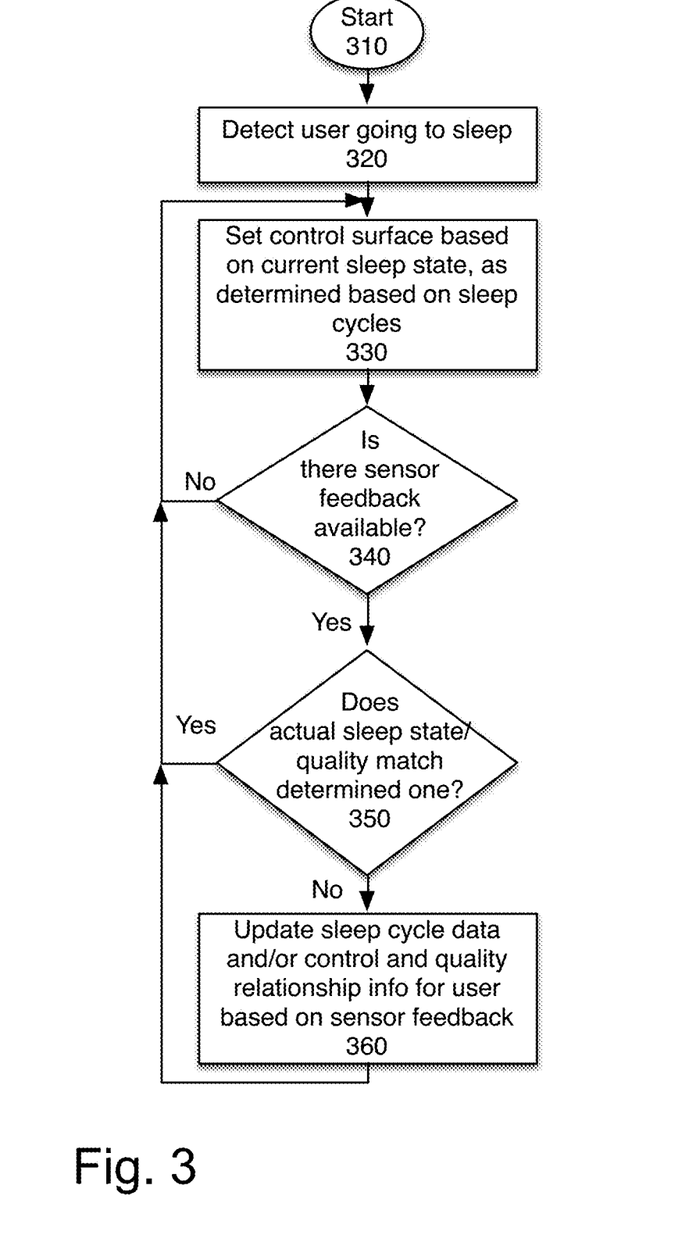
FIG. 3 is an overview flowchart of one embodiment of the feedback loop in the system.

FIG. 3 is an overview flowchart of one embodiment of the feedback loop in the system. The system starts at block 310. In one embodiment, the system starts when the sleeping surface system is initialized.

At block 320, the system detects that the user is going to sleep. In one embodiment, this may be done by detecting using one or more sensors that the user's movement patterns or brain waves reflect that the user is going to sleep. In one embodiment, a simple pressure sensor, proximity sensor, camera, or weight sensor may be used. In one embodiment, when more complete sensor data is not available, the system determines that the user goes to sleep a preset number of minutes after the user is identified as getting into bed.

At block 330, the system sets the controlled sleeping surface based on the current sleep state, as determined based on the sleep cycle data. In one embodiment, this may be normative sleep data. Alternatively, this may be customized sleep data, based on the user's personal sleep patterns.

At block 340, the process determines whether there is sensor feedback available, to validate the user's current sleep phase. If no sensor feedback is available, the process returns to block 330, to continue controlling the controlled sleep surface based on the predicted sleep cycles.

If sensor feedback is available, the process continues to block 350. At block 350, the process determines whether the actual sleep state and sleep quality match the automatically determined one. If so, the process returns to block 330, to continue setting the controlled sleeping surface based on the sleep cycle data.

If the system determines that the actual sleep cycle or sleep quality does not match the predicted sleep phase/quality, the process continues to block 360.

At block 360, the system updates the sleep cycle data and/or control and quality relationship data information for the user, based on the sensor feedback. In one embodiment, the adjustment is also stored for later review and potential adjustment of the user sleep cycles. The process then returns to block 330, to set the control surface based on the adjusted sleep cycle data.

In this way, the controlled sleep surface is continuously adjusted to support the user's optimal sleep cycles. The system works when sensors are available to provide instant feedback, and also when no such sensor data is available. Thus, the standard single-temperature sleep surface is replaced by a sleep-phase optimized controlled sleeping surface.

Figure 4:
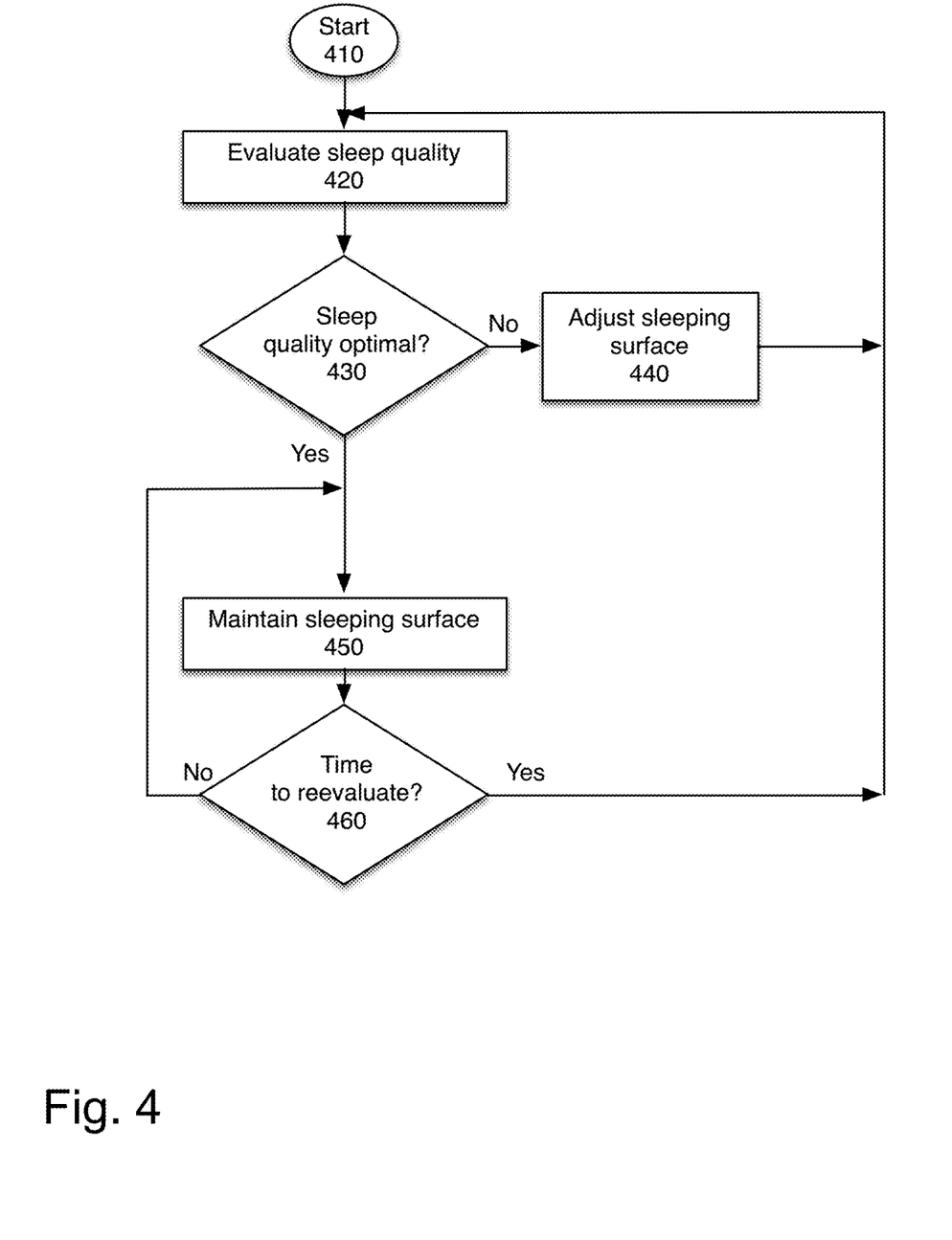
FIG. 4 is a flowchart of one embodiment of the feedback system.

FIG. 4 is a flowchart of one embodiment of the feedback system, when the monitoring system is fully online. The process starts at block 410. In one embodiment, this process is continuously available when the user is utilizing the controlled sleep surface.

At block 420, the system evaluates the user's sleep quality. The sleep quality reflects the user's current sleep phase as well as how well the user is sleeping overall.

At block 430, the process determines whether the sleep quality is optimal. In one embodiment, an optimal sleep quality is the user being in the correct sleep phase, and sleeping well.

If the sleep quality is not optimal, the process, at block 440, adjusts the sleeping surface. In one embodiment, this may involve changing the temperature and/or firmness of the sleeping surface. Other changes may be made, as well. The process then returns to block 420, to evaluate the adjusted sleep quality.

When the sleep quality is optimal, the process continues to block 450, and the sleeping surface is maintained. At block 460, the process determines whether it is time to reevaluate. If not, the process continues to maintain the sleeping surface, at block 450. If it is time to evaluate, the process returns to block 420, to reevaluate the sleep quality. In one embodiment, the timer reevaluates the user's sleep quality every few minutes. In another embodiment, the timer reevaluates the user's sleep quality at an interval designed to coincide with the expected sleep phases. In one embodiment, the user's sleep quality would be reevaluated when the user would be expected to start shifting to the next sleep phase, and then more frequently during the phase change, and less frequently when in a particular sleep phase.

Figure 5:
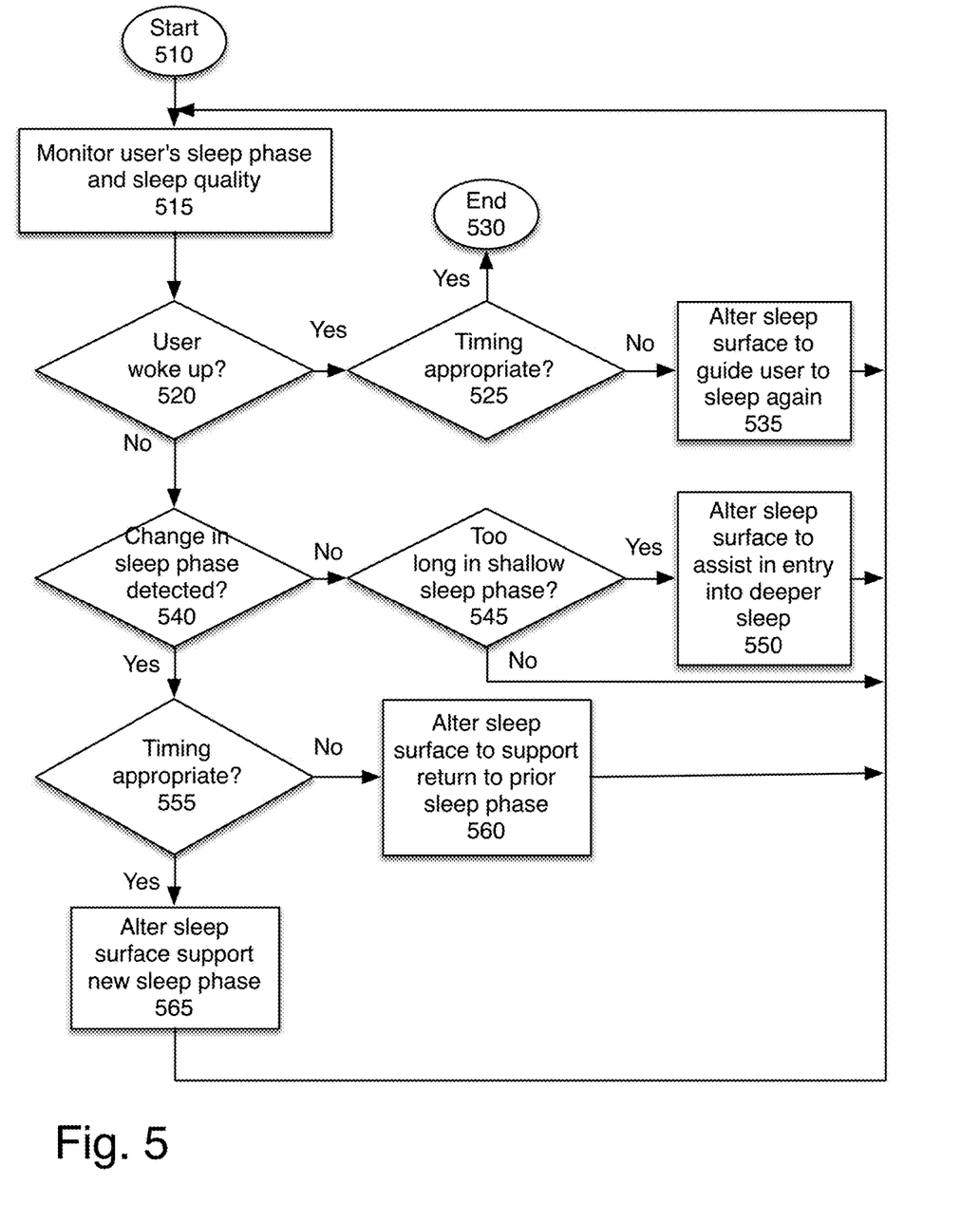
FIG. 5 is a flowchart of one embodiment of the monitoring and adjustment.

FIG. 5 is a flowchart of one embodiment of the monitoring and adjustment. The process starts at block 510. In one embodiment, this process starts when the system determines that the user is sleeping on the controlled sleeping surface.

At block 515, the user's sleep phase and sleep quality are monitored. As noted above, this may be done by a plurality of sensors in a monitoring system or integrated with the sleep surface itself.

At block 520, the process determines whether the user woke up. If so, the process, at block 525, determines whether the timing is appropriate for the user to wake up. The timing would be considered appropriate if an alarm is set, it is morning and the user sleeps a standard night schedule, the user has slept a standard night's sleep or a set number of complete sleep cycles, or the user's calendar indicates that the user should be waking up, in one embodiment. If the timing is appropriate, the process ends, at block 530, and the user remains awake, and presumably exits the controlled sleep surface.

If the timing is considered to be not appropriate, the process continues to block 535. At block 535, the sleep surface is altered, to assist the user in falling back asleep. For example, while sleeping is generally more refreshing on a cooler surface, many people find it easier to initially fall asleep on a warmer, softer surface. Therefore, at block 535, the sleep surface is adjusted to ease falling asleep. The process then returns to block 515, to monitor the user's sleep phase and sleep quality.

If the user did not wake up, the process continues to block 540. At block 540, the process determines whether a change in the user's sleep phase was detected. If no change in the sleep phase is detected, the process determines, at block 545, whether the user has been too long in a shallow sleep phase. For optimal sleep quality, the user should spend time in the deep sleep phase, though REM sleep is necessary as well. If the user has not spent too long in a shallow sleep phase, the process returns to block 515 to continue evaluating the user's sleep quality.

If the user has been in a shallow sleep phase too long, the sleep surface is altered to assist entry into deeper sleep, at block 550. The process then continues to monitor the user's sleep quality.

If a change in the sleep phase was detected, at block 540, the process continues to block 555. At block 555, the process determines whether the change in sleep phase is appropriately timed. As noted above, it is better to spend longer time in deep sleep. If the timing is not appropriate, at block 560 the sleep surface is altered to support return to the prior sleep phase. If the timing is appropriate, the sleep surface is altered, if needed, to support the new sleep phase, at block 565. The process then returns to block 515 to continue monitoring the user's sleep phase and sleep quality.

Note that although this process is described only with respect to adjusting the sleep surface, any other environmental factors may also be concurrently adjusted. Such environmental factors may include sounds (e.g. a white noise generator, sound generator or the like), smells, light level, etc. In one embodiment, the system may interact with external controls to optimize the user's sleep environment, in addition to optimizing the user's controlled sleep surface.

Figure 6:
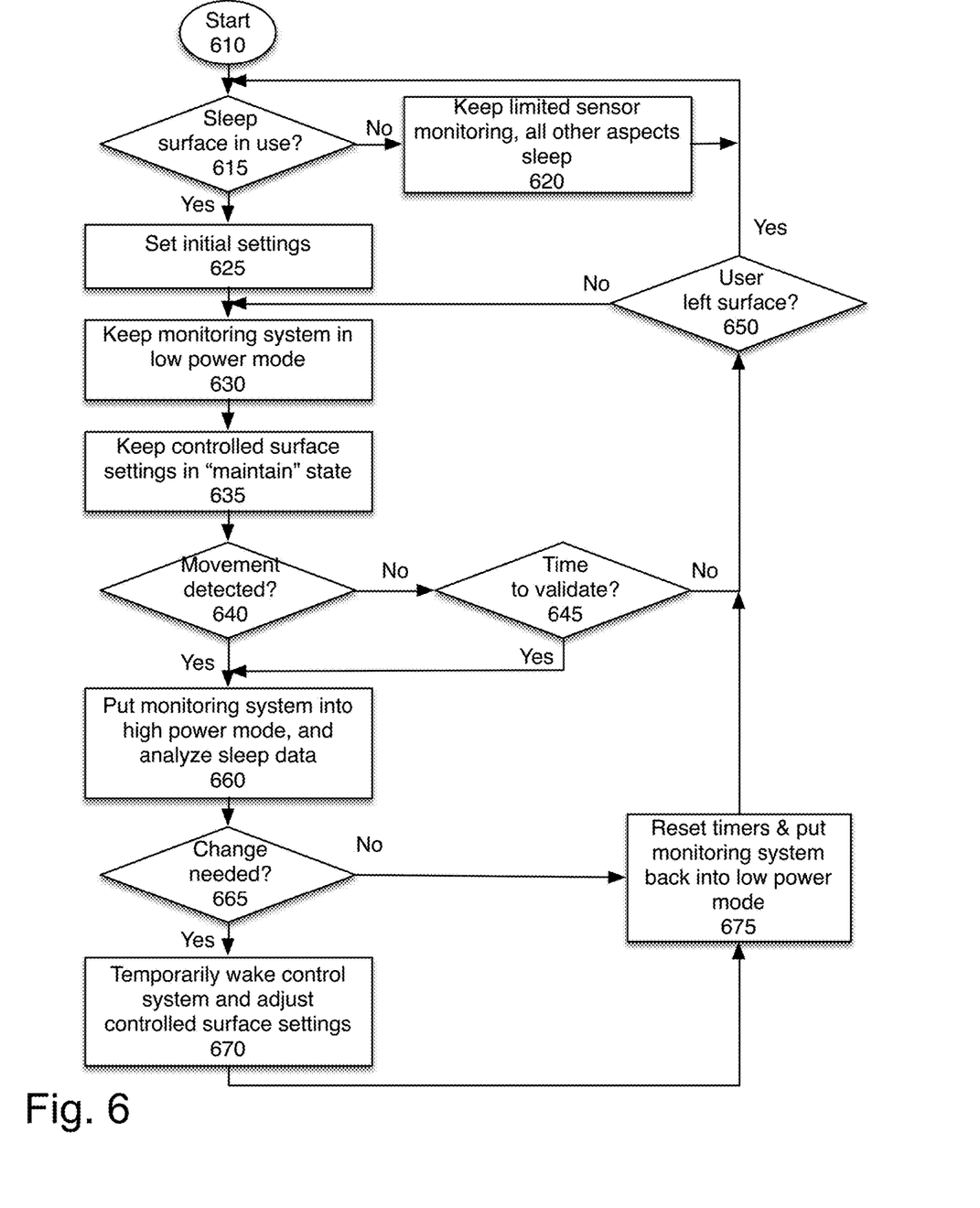
FIG. 6 is a flowchart of one embodiment of low-power use in the system.

FIG. 6 is a flowchart of one embodiment of low-power use in the system. The process starts at block 610. In one embodiment, this process is used whenever the sleeping surface and/or the monitoring system is active.

At block 615, the process determines whether the sleeping surface is in use. The sleeping surface is in use if a user is sleeping or laying on it. If the sleeping surface is not in use, at block 620, the process keeps a limited sensor monitoring awake, while all other aspects of the system are placed in a sleep mode or turned off. In one embodiment, the limited sensor monitoring may be one or more of: a motion sensor, a pressure or touch sensor, a weight sensor, or another sensor capable of detecting a user on the sleeping surface. This enables the system to detect when it needs to be turned back on to monitor the user, but save power when the user is not utilizing the sleeping surface.

If the sleeping surface is in use, the process continues to block 625. At block 625, the initial settings are set for the sleeping surface. These initial settings, in one embodiment, are settings optimized to enable a user to fall asleep.

At block 630, the monitoring system placed back into, and maintained, in a low power mode. At block 635, the controlled surface settings are also maintained in the "maintain" state. The maintain state, in this context, means the state set by the system. So the temperature and firmness may be maintained at a particular level.

At block 640, the process determines whether movement is detected. Movement, in this context means movement above a threshold, which is likely to indicate a change in the user's sleep state or sleep quality. In one embodiment, micro-movements would not trigger this.

If no movement is detected, the process determines whether it is time to validate the current settings. If it is not yet time to validate the current setting, the process continues to block 650. At block 650, the process determines whether the user has left the sleeping surface, if so, the process returns to block 615, to monitor whether the sleeping surface is in use and maintain all but a minimum number of sensors in a sleep state. If the user did not leave the surface, at block 650, the process returns to block 630, to keep monitoring the system in a low power mode.

If at block 640, movement was detected, or the system determined that it was time to validate, at block 645, the process continues to block 660.

At block 660, the monitoring system is placed into a higher power mode, and the sleep data collected during the low power monitoring phase is analyzed. In one embodiment, this analysis may be done locally, or remotely. If it is done remotely, in one embodiment, only the communication system and elements needed to send data and receive analysis, are placed in a higher power state.

At block 665, the process determines based on the analysis whether the controlled sleep surface needs to be adjusted. If it needs to be adjusted, at block 670, the control system is temporarily woken, and the controlled surface settings are adjusted, as determined by the monitoring system's analysis. The process then continues to block 675. If no change is needed, as determined at block 665, the process continues directly to block 675.

At block 675, the timers are reset, and the monitoring system is placed back into a low power mode. The process then continues to block 650, to verify that the user remains on the surface, and to either go into sleep/off mode or continue monitoring in low power mode. In this way, the system can provide close monitoring and nearly instant reaction, while minimizing power consumption of the monitoring and control systems.

Figure 7:
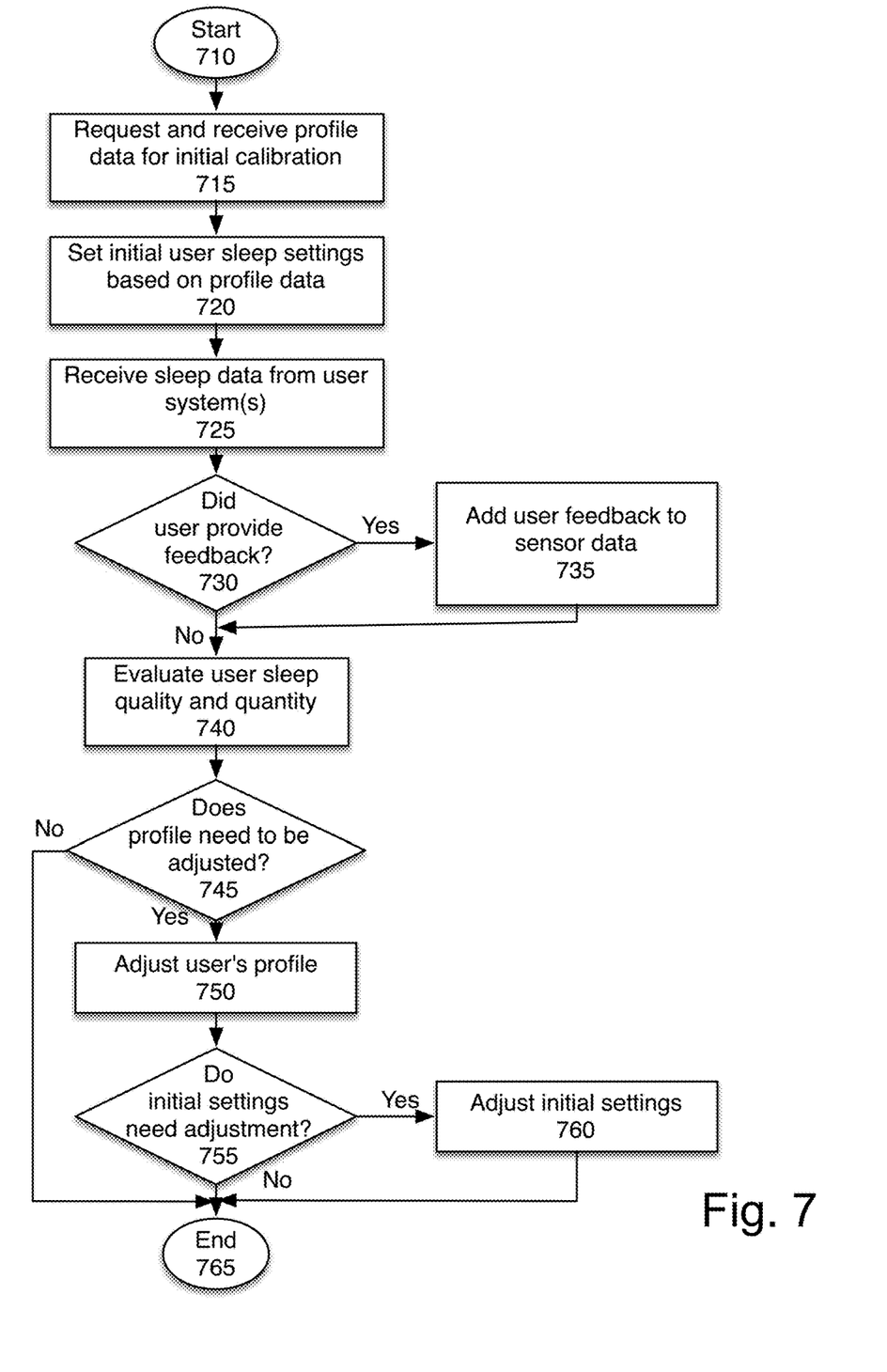
FIG. 7 is a flowchart of one embodiment of adjusting the parameters of the system.

FIG. 7 is a flowchart of one embodiment of adjusting the parameters of the system. The process starts at block 710. In one embodiment, this process is initiated when the user first starts using the controlled sleeping surface.

At block 715, user data is requested and received, for initial calibration. In one embodiment, the user is asked certain standard questions that may impact his or her sleep patterns. Questions may include the user's gender, age, height, weight, and any relevant medical conditions, e.g., diabetes, high blood pressure, etc. In one embodiment, if the monitoring system is an integrated system that is used for other user monitoring, this data may be obtained from the monitoring system rather than directly from the user.

The initial sleep settings are set, at block 720, based on the profile data. In one embodiment, these initial sleep settings are associated with the controlled sleeping surface itself, rather than just with the monitoring system.

At block 725, the system receives sleep data from the user system. This is obtained when the user starts utilizing the controlled sleeping surface. This data is the data collected by the monitoring system, about the user's sleep phases and sleep quality.

At block 730, the process determines whether the user provided feedback about their sleep experience. In one embodiment, the user can opt to provide feedback. The feedback may be as general as "slept well" or as specific as "took a long time to fall asleep, woke up multiple times, had bad dreams, woke up in bad mood, overall slept badly." In one embodiment, the feedback may be provided using a feedback menu. In on embodiment, the feedback may be provided verbally, and the system interprets the feedback and classifies the feedback.

If feedback was provided, at block 735 the user feedback is added to the sensor data, used to evaluate the user sleep quality and quantity.

At block 740, the system uses the available data, sensor data and/or user feedback, to evaluate the user's sleep quality and quantity.

At block 745, the process determines whether the user's profile should be adjusted. The user's profile defines the default sleep patterns for the user. Additionally, the user's profile is used in a cumulative evaluation for users of the same type, to optimize a normative data set.

If no adjustment is needed, the process ends at block 765.

If an adjustment is needed, the process at block 750 adjusts the user's profile. In one embodiment, the user's profile, over time, is more and more detailed. In addition to the user's basic description, the system may include data about historical sleep quality and correlative factors. For example, the system may identify that when the user goes to sleep after midnight, he or she sleeps more shallowly and needs a harder sleep surface to sleep well. Additional relevant correlations may also be identified. In one embodiment, in addition to adjusting the system itself, the system may also inform the user of these correlations. The user may, then, be encouraged to go to sleep before midnight, or to close the blinds, or perform some other act that the system cannot control. In one embodiment, if the monitoring system or computer system also has monitoring data from other sources, e.g. from daily monitoring of the user, additional correlations may also be identified. For example, the system may determine that the user prefers a harder/softer/hotter/colder sleeping surface after a vigorous workout, than on a day that did not include such a workout. Such additional adjustments may also be taken into consideration.

At block 755, the process determines whether the initial settings should be adjusted based on this data. If so, at block 760, these initial settings are adjusted. The process then ends. In one embodiment, these adjustments are also provided as feedback to a central server.

Over time, and with many users' data, the central server may adjust the default settings for various user types. User types may be found to be the standard user groupings (e.g. gender, age, height, and weight). In one embodiment, the system may additionally identify other relevant groupings. Some exemplary groupings that may be identified may be based on athleticism, work environment, schedule, caffeine consumption, vegetarianism or other eating habits, having children, etc. It should be noted that these groupings are merely exemplary, and other types of groupings may also be identified. In one embodiment, as additional user groupings are identified, in one embodiment the initial profile data requested may be adjusted to account for these identified groupings. In this way, over time, the user's own system is customized for the user, and the default initial settings are more and more precisely subdivided based on user characteristics.

Figure 8:
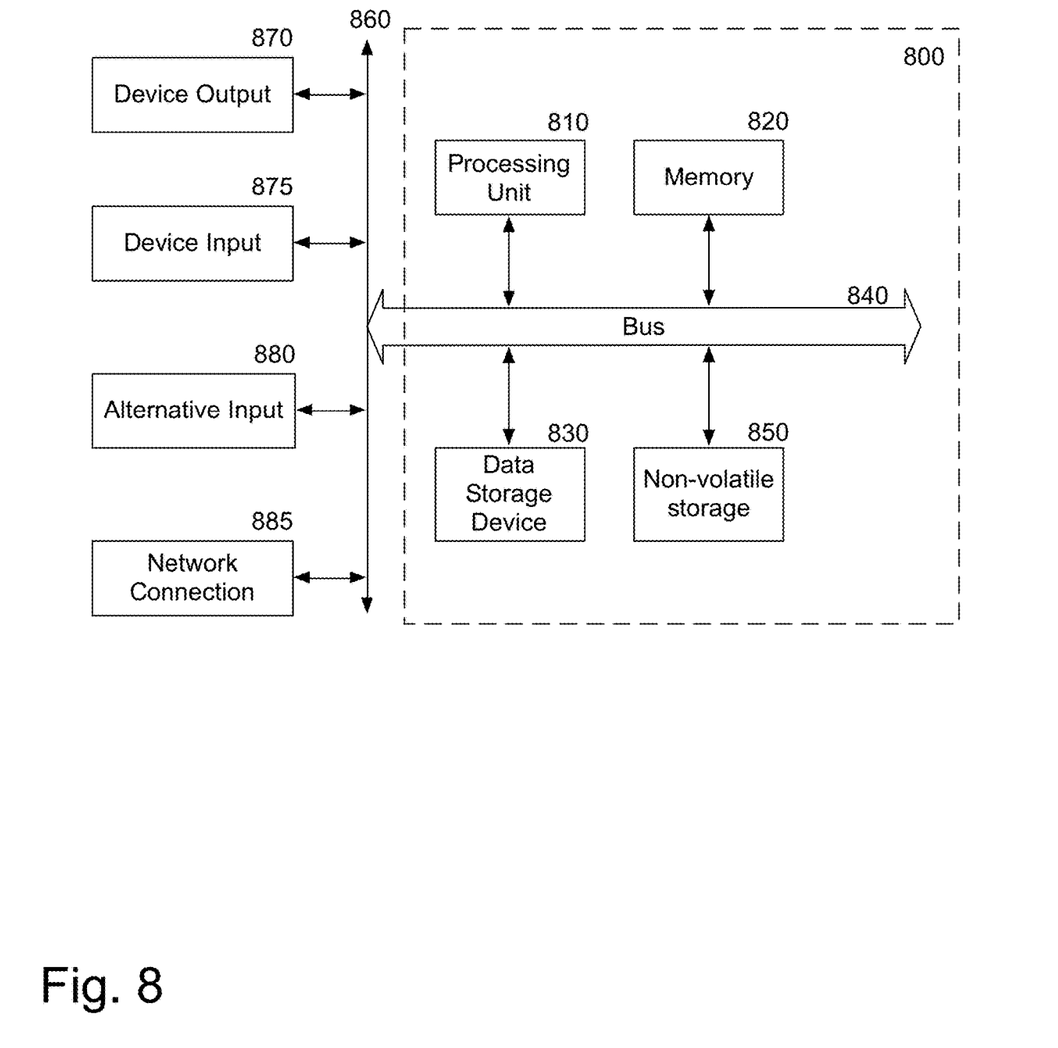
FIG. 8 is a block diagram of one embodiment of a computer system that may be used with the present invention.

FIG. 8 is a block diagram of a particular machine that may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment, the system also includes a data storage device 830 such as a magnetic disk or optical disk and its corresponding disk drive, or Flash memory or other storage, which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g. vibrations, etc.)

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, wireless network, or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 840, the processor 810, and memory 850 and/or 820.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 810, a data storage device 830, a bus 840, and memory 820, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine-readable medium includes read-only memory (ROM), random access memory (RAM), magnetic disk storage media, optical storage media, flash memory devices, or other storage media that may be used for temporary or permanent data storage. In one embodiment, the control logic may be implemented as transmittable data, such as electrical, optical, acoustical, or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A controlled sleeping surface, comprising:
   storage for storing a precalculated user-specific optimal sleep rhythm for a user based one or more user characteristics of the user, the user characteristics comprising the user's age, gender, weight, and height;
   an identity determiner to determine an identity of a user on the controlled sleeping surface based on sensors of the controlled sleeping surface and to obtain the precalculated user-specific optimal sleep rhythm of the user from the storage for the identified user;
   a processor to determine an effective temperature for the user based on one or more of the user characteristics of the user and to determine a relative temperature for the user based on the effective temperature and on at least one sleeping condition of the user;
   a monitoring system to determine an actual sleep state of the user on the controlled sleeping surface;
   sleep phase logic to determine a current optimal sleep state of the user on the controlled sleeping surface based on the actual sleep state of the user and the precalculated user-specific optimal sleep rhythm of the user; and
   a controller to adjust a firmness of the controlled sleeping surface based on the determined current optimal sleep state of the user, the controller further to adjust a temperature of the controlled sleeping surface based on the current optimal sleep state of the user, the effective temperature, and the relative temperature.

2. The controlled sleeping surface of claim 1, further comprising a user customizer that adjusts the precalculated user-specific optimal sleep rhythm of the user based on a feedback loop receiving the actual sleep state of the user and input from the sensors.

3. The controlled sleeping surface of claim 1, wherein the controlled sleeping surface comprises a mattress having a heating and a cooling facility, to enable a temperature of the mattress to be set for optimal sleep quality.

4. The controlled sleeping surface of claim 1, wherein the monitoring system is further configured, when an additional user is on the controlled sleeping surface with the user, to determine the identity of the user and the additional user on the controlled sleeping surface, based on two or more of the user's and the additional user's weight, blood pressure, heart rate, or movement patterns.

5. The controlled sleeping surface of claim 1, wherein the actual sleep state is determined based on the obtained pre-calculated sleep rhythm of the user when a sleep state cannot be obtained from the sensors.

6. The controlled sleeping surface of claim 1, wherein the sensors further comprise:
   a sensor selected from among: a camera, pressure sensor, proximity detector, anaccelerometer, a gyroscope, a light sensor, blood oxygen sensor, blood pressure/heartrate sensor, temperature sensor, a weight sensor surface, or motion sensor to detect the user on the controlled sleeping surface, or a user interface utilized by the user to indicate that the user is going to sleep.

7. The controlled sleeping surface of claim 1, wherein the obtained pre-calculated sleep rhythm is a sleep rhythm, based on data of the user's prior sleep cycles.

8. The controlled sleeping surface of claim 1, wherein the monitoring system comprises:
   a sensor system configured to detect physiological data of the user; and a processor configured to implement an analysis system to use the
   physiological data from the monitoring system to determine a user's sleep state and sleep quality.

9. The controlled sleeping surface of claim 8, wherein the physiological data of the user includes motion data, the motion data used to identify sleep state.

10. The controlled sleeping surface of claim 1, wherein the controller further adjusts temperatures for a plurality of zones, corresponding to body parts of the user.

11. The controlled sleeping surface of claim 1, further comprising differential temperature controls for a single sleeper vertically, comprising differential temperature controls for at least two of the user's head, torso, legs, and feet.

* * * * *